United States Patent [19]

Brown

[11] Patent Number: 4,608,977
[45] Date of Patent: Sep. 2, 1986

[54] SYSTEM USING COMPUTED TOMOGRAPHY AS FOR SELECTIVE BODY TREATMENT

[76] Inventor: Russell A. Brown, 2826 South 2420 East, Salt Lake City, Utah 84109

[21] Appl. No.: 450,955

[22] Filed: Dec. 20, 1982

Related U.S. Application Data

[63] Continuation of Ser. No. 70,571, Aug. 29, 1979, abandoned.

[51] Int. Cl.$^4$ .............................................. A61B 17/00
[52] U.S. Cl. ................... 128/303 B; 128/630; 378/208; 378/162
[58] Field of Search ..................... 128/303 B, 660, 630; 378/208, 20, 162–164

[56] References Cited

U.S. PATENT DOCUMENTS

| | | | |
|---|---|---|---|
| 3,508,552 | 4/1970 | Hainault | 128/303 B |
| 4,230,117 | 10/1980 | Anichkov | 128/303 B |
| 4,341,220 | 7/1982 | Perry | 128/303 B |
| 4,386,602 | 6/1983 | Sheldon et al. | 128/303 B |

Primary Examiner—C. Fred Rosenbaum
Assistant Examiner—Gene B. Kartchner
Attorney, Agent, or Firm—Nilsson, Robbins, Dalgarn, Berliner, Carson & Wurst

[57] ABSTRACT

A system utilizing computed tomography (CT) as for surgery. A CT scanner provides data representative of or slices taken through a body member. Display apparatus reveals the slices. A reference apparatus (frame) affixed to the body, operates in conjunction with the scanner and the display apparatus. The frame includes: structure for affixation to the body, holder means for guiding the therapeutic instrument, and structure for providing reference indications. The system further includes a data processing structure and control means for transforming data between frame coordinates and slice coordinates.

31 Claims, 5 Drawing Figures

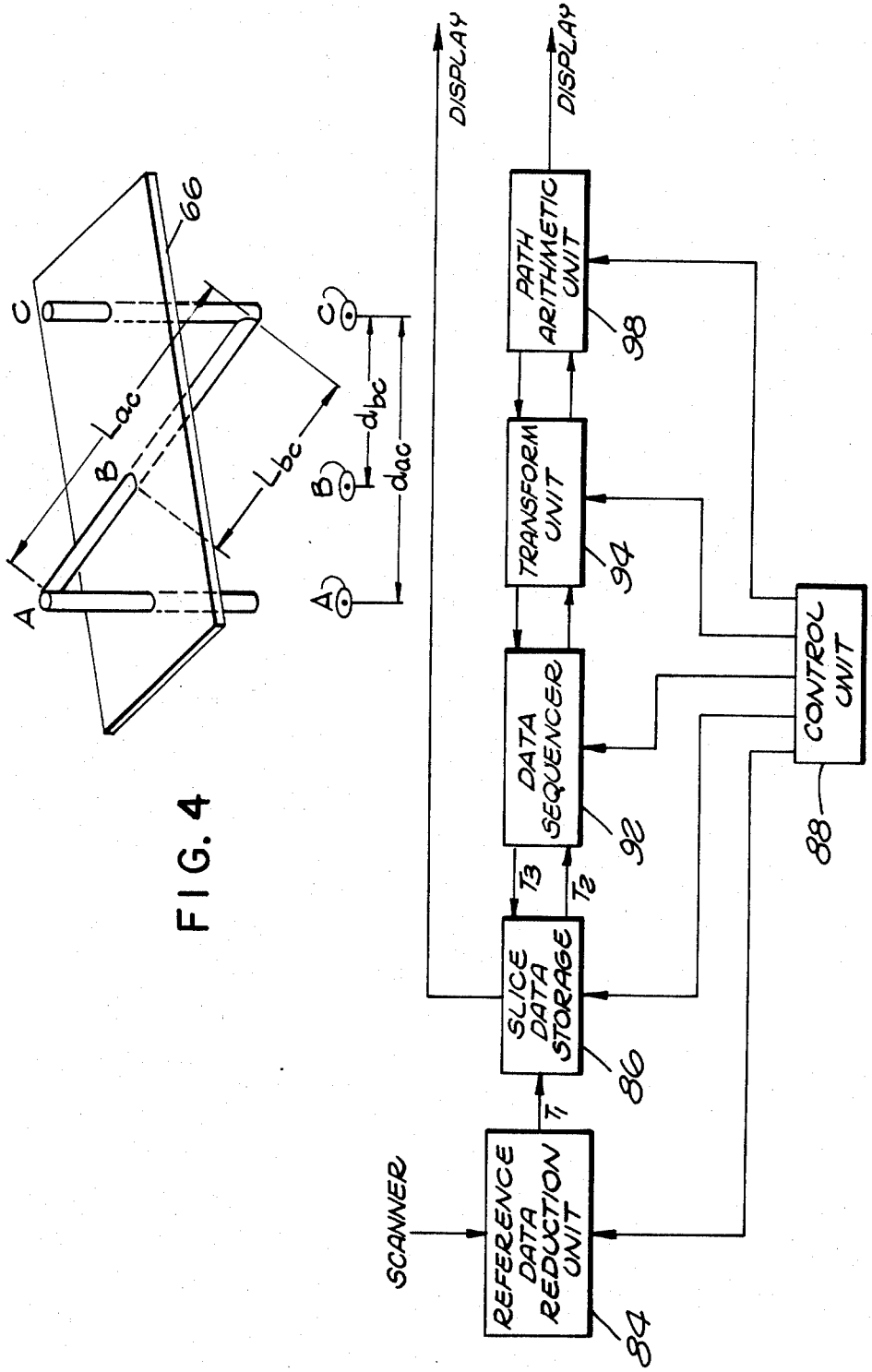

SYSTEM USING COMPUTED TOMOGRAPHY AS FOR SELECTIVE BODY TREATMENT

This is a continuation of application Ser. No. 070,571, filed Aug. 29, 1979, now abandoned.

BACKGROUND AND SUMMARY OF THE INVENTION

Computed tomography (CT) systems are effective to provide data from the interiors of the body which can be reduced to displays without the complications of superimposed detail normally inherent in traditional x-ray pictures. For example, CT scanners are in widespread use providing brain information that is very useful both in diagnosis and treatment. Details of the structure and operation of such scanners are provided in U.S. Pat. No. 3,106,640 issued Oct. 8, 1963, and entitled "Radiant Energy Apparatus for Investigating Selected Areas of the Interior of Objects Obscured by Dense Material".

A CT scan might, for example, be taken of a patient evidencing symptoms of a brain tumor. Essentially, the actual information is representative of a plurality of individual data planes or scan slices which are taken through the brain and are somewhat parallel, depending upon the degree to which the patient's head may have moved between the individual scans. Studying the scan slices, the trained physician or the like may observe the presence and approximate location of a tumor. With such information, a variety of treatments might be effectively executed, several of which involve placing an instrument or probe into the brain so that the probe tip is at the tumor or target location.

Although the CT scanner provides exceedingly valuable information, a problem has remained of accurately defining the position of the target with respect to an accessible reference location for accurately placing a therapeutic probe. At least one locating method has been proposed and was described in the *American Journal of Roentgenology*, Volume 127, pages 167–170, 1976, by Bergstrom and Greitz entitled "Stereotaxic Computed Tomography". However, such prior technique requires that the patient's head be fixed to the CT scanner to preserve the reference. Such a requirement not only imposes considerable discomfort on the patient, but results in other inconveniences, particularly if surgical procedures are involved. Consequently, a need exists for a system utilizing a CT scanner to locate and reach internal maladies which system does not rely upon a mechanically fixed relationship between the patient and the CT scanner. Such a system is needed that will enable the accurate and reproducible location of a target point and which facilitates the determination of a path to a target as well as providing for guidance of a probe along such a path.

In general, the present invention includes a stereotactic frame which is affixed to the patient, yet will allow the patient freedom of motion and relative comfort. The stereotactic frame cooperates with the CT scanner to provide data to reference each scan slice to the stereotactic frame. Additionally, the stereotactic frame incorporates a universal holder mechanism for guiding a therapeutic probe to a target. Using the stereotactic frame as an integral component, the system of the present invention also incorporates a CT scanner along with a display apparatus and data processing means for transforming and processing data.

Considering an exemplary use of the system, the stereotactic frame would be fixed to a patient's cranium for cooperative use with a CT scanner to accomplish a brain scan containing reference indicia. At the conclusion of the brain scan, the patient (wearing the stereotactic frame) would be mobile and could move from the CT scanner. The scan slices then would be displayed by the system for study and analysis to determine the presence and location of a tumor (target). The target is indicated to the system (as by a cursor input to a specific scan slice) along with a second point to supplement the data and designate a path for reaching the tumor. Using the reference indicia, the data processing apparatus expresses the path in terms that are referenced to the stereotactic frame. For example, the path may be indicated by position settings or positional indications for the holder mechanism on the stereotactic frame. The computing apparatus in cooperation with the display apparatus then indicates the penetration location of the path through each scan slice. If problem penetrations are indicated, an alternate path is selected. If the path under investigation appears relatively free of complications, the patient is taken to surgery; and using the stereotactic frame, a therapeutic probe is guided to the target with minimal disturbance of tissue along the path.

BRIEF DESCRIPTION OF THE DRAWINGS

In the drawings, which constitute a part of this specification, an exemplary embodiment demonstrating the various objectives and features hereto is set forth as follows:

FIG. 4 is a diagrammatic view illustrative of the operation of a portion of the frame of FIG. 3 as an integral part of the system of FIG. 1; and FIG. 5 is a block diagram of an exemplary computing apparatus as may be embodied in the system of FIG. 1.

DESCRIPTION OF ILLUSTRATIVE EMBODIMENT

As indicated above, a detailed illustrative embodiment of the invention is disclosed herein. However, embodiments may be constructed in accordance with various forms, some of which may be rather different from the disclosed illustrative embodiment. Consequently, the specific structural and functional details disclosed herein are merely representative, yet in that regard they are deemed to provide the best embodiment for purposes of disclosure and to provide a basis for the claims herein which are advanced to define the scope of the present invention.

Figure 1:
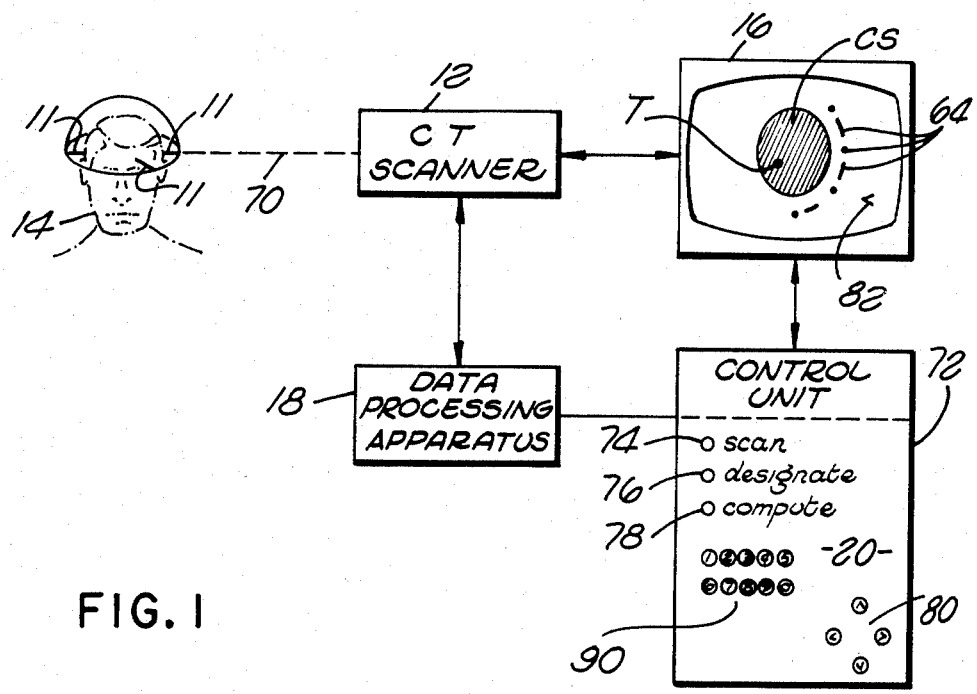
FIG. 1 is a block and schematic diagram of a system constructed in accordance with the present invention.

Referring initially to FIG. 1, a stereotactic frame 10 is represented for use in cooperation with a CT scanner 12. In general, the frame 10 is affixed to the body by fasteners 11, specifically in the form as illustrated, to the cranium of a patient 14, indicated in phantom. The frame 10 and patient 14 are sensed by a radiation pattern from the scanner 12 to provide sets of data representative of individual planes called scan slices. Scan slice data is supplied from the scanner 12 to a console 16 which displays individual scan slices for visual study.

In general, the structure of the CT scanner 12 along with that of the console 16 is well known in the prior art, several manufacturers having introduced systems in which scan slices are displayed, as recognized in a relevant article appearing in the *Journal of Computer Assisted Tomography*, Volume 2, pages 368-371, July 1978, entitled "A Device to Indicate Anatomical Level in Computed Tomography".

In accordance with the present invention, the data of individual scan slices is processed by a data processing apparatus 18 which, along with the other components of the system, is commanded by a control unit 20. Computation is performed to: (1) determine a probe path, (2) transform data coordinates, and (3) determine and indicate each penetration by the probe path through individual scan slices. These operations are sequenced and controlled by a panel 20 acting on a control unit (discussed below) as related to the apparatus 18.

It is important to realize that the stereotactic frame 10 need not be physically connected to the CT scanner 12. That is, while the frame 10 (along with the patient 14) occupies a position of sensing relationship with the scanner 12, the patient 14 (carrying the frame 10) need not be locked mechanically to the scanner 12. After completion of the brain scan, the patient 14 is mobile and can be removed from the scanner 12, though retaining the frame 10, as for subsequently guiding the placement of a therapeutic probe. Also, note that the probe may actually be guided by the frame with the frame still in the scanner. Then scans can be taken to verify correct probe position.

Figure 2:
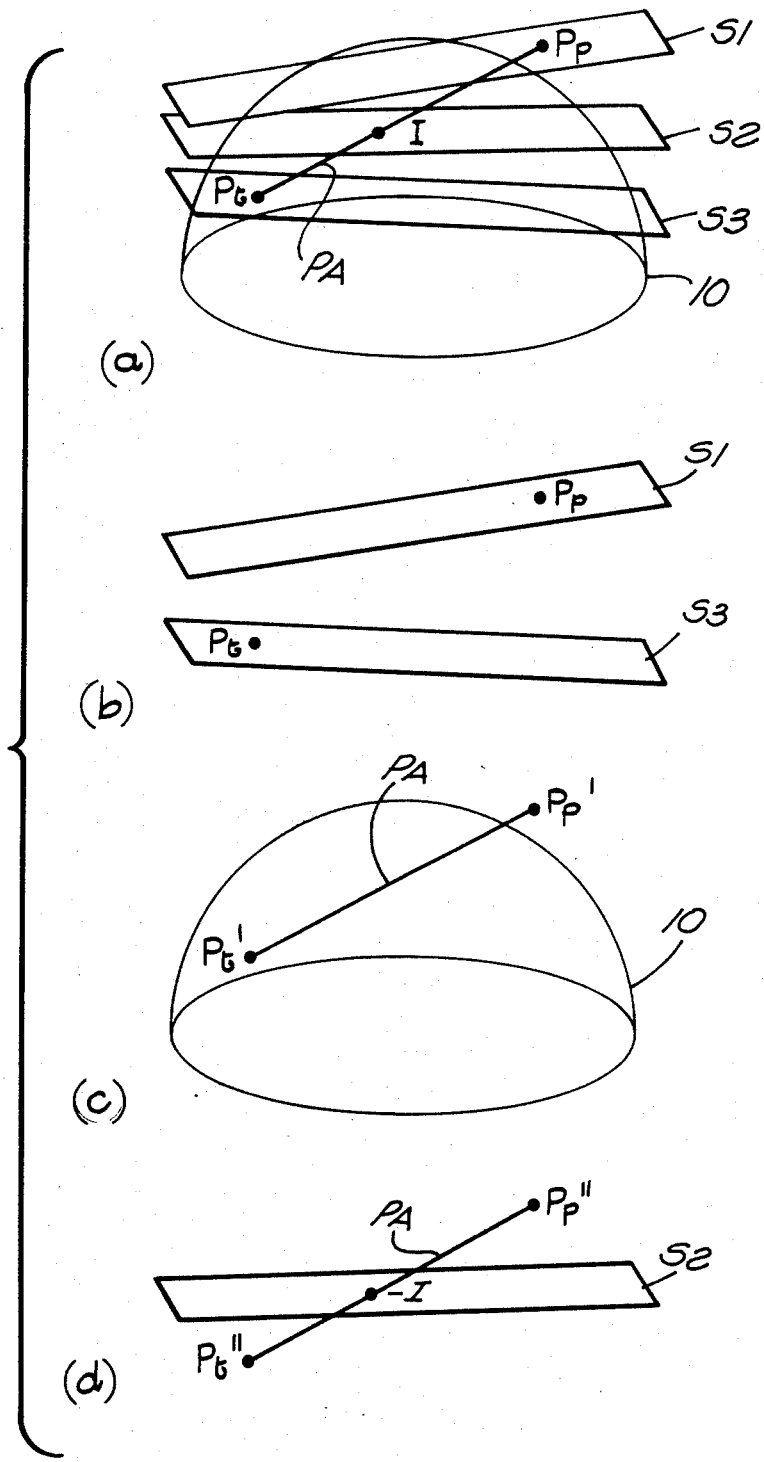
FIG. 2 is a series of diagrammatic views illustrative of the operation of the system of FIG. 1.

At this point, to advance an understanding of the system of the present invention, some graphic considerations are pertinent for illustrating the operations in somewhat greater detail. Referring to FIG. 2, the frame 10 is represented diagrammatically along with scan slices in a set of related drawings. No patient is illustrated in FIG. 2; however, it is to be understood that the frame 10 would be affixed to a patient so that scan slices taken through the frame 10 would contain diagnostic information.

Referring to FIG. 2(a), three somewhat parallel scan slices S1, S2, and S3 are repesented to pass through the frame 10. Considering the stereotactic frame 10 as a hemisphere, the scan slices S1, S2, and S3 are generally parallel to the plane defined by the base of the hemisphere. However, as the patient's head is not locked to the scanner 12 (FIG. 1) movement occurring between individual scan slices results in different positions for the slices as indicated (perhaps to some extreme) by the divergence of the slices S1, S2, and S3. In any event, the data for each of the slices is individual. In accordance herewith, the data includes physiological data as well as reference data resulting from reference apparatus on the frame 10 (not shown in FIG. 2) for locating the position of each slice with reference to the frame 10.

After scan slices have been taken (exemplified by the slices S1, S2, and S3), each slice may be displayed as a cross section CS (FIG. 1) by the console 16. Assume, for example, that the slice S3 (FIG. 2(a)) is displayed exhibiting a tumor T that is defined as the target $P_t$ for a therapeutic probe. After such a determination, the target $P_t$ can be designated (as described below) in the slice S3 (FIG. 2(b)). Additionally, a point $P_p$ is designated in the slice S1 to define a path PA for a therapeutic probe that will extend from outside the frame 10 to the target $P_t$.

After the path PA has been determined (as two points $P_t$ and $P_p$, in scan slices S1 and S3, FIG. 2(b)), the data is processed to reference the path PA to the frame 10. That is, the points $P_t$ and $P_p$ (in scan slice coordinates) are transformed to provide the points $P_t'$ and $P_p'$ (FIG. 2(c)) in coordinates referenced to the frame 10. The frame-referenced coordinates for the points $P_t'$ and $P_p'$ are then utilized to compute the settings for the probe holder or guide, for placing the tip of a therapeutic probe at the target T (defined as either $P_t$ or $P_t'$). However, prior to such placement, using the system hereof the potential dangers of the proposed probe path are investigated. Specifically, the penetration points of the path, for each scan slice, are transformed to the coordinates of such slice so that the puncture locations can be considered. Thus, as indicated in FIG. 2(d), the points $P_t''$ and $P_p''$ are developed for each scan slice to display the intersect I. Accordingly, indications of any troublesome punctures in scan slices along the path PA are indicated so that an alternate path can be considered.

Figure 3:
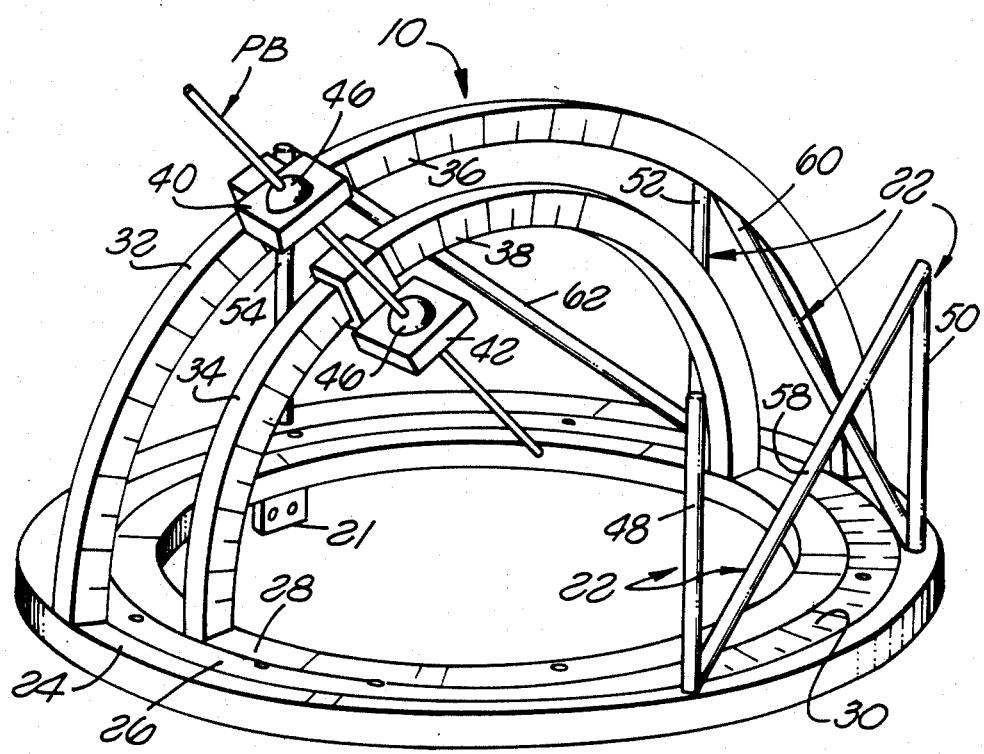
FIG. 3 is a perspective view of an exemplary form of stereotactic frame which may be embodied in the system of FIG. 1.

In view of the above preliminary explanation, a detailed consideration of the frame 10 as depicted in FIG. 3 is deemed now to be appropriate. The exemplary frame of FIG. 3 has been produced in acrylic plastic to be rigidly attached to the patient's cranium, as with screw devices that extend through fastener brackets 21. The frame is worn during the operating period of the CT scanner and remains attached until surgery is complete. The frame 10 guides a therapeutic probe PB to reach any desired point inside the frame from various directions. The probe PB is held and selectively guided after a holder mechanism is set to reflect a selected path. The settings for the holder mechanism are computed by the system to establish a specific direction for accomplishing a predetermined path. The penetration of the probe PB is also computed and is executed accordingly.

In summary, it is to be understood that in addition to the holder mechanism, the frame 10 includes two other functional structures. The structure for affixing the frame 10 to the cranium is relatively simple and direct. The reference structure, which is of material to be sensed by the scanner, for providing landmarks in each scan slice and which allows the system to transfer information from the slice coordinate system to the frame coordinate system, generally takes the form of a series of rods 22.

Considering the structural details of the frame 10, three concentric slidingly mated rings 24, 26, and 28 provide the base. The middle ring 26 bears indicia 30 for measuring the angular offset of the other two rings 24 and 28 from reference positions. Thus, the ring 26 carries fastener brackets 21 to be affixed to the patient's cranium as a stable reference.

The external ring 24 supports an outer perpendicular arch 32 while the internal ring 28 supports an inner perpendicular arch 34. Approximately one-half (some ninety degrees) of each of the arches carry scale markings 36 and 38, each for indicating the position of a probe holder 40 or 42, respectively, which are structurally similar. The probe holders 40 and 42 are slidably carried on the arches 32 and 34, respectively, and each holder defines an annulus for receiving a ball 46 that may be freely revolved therein.

The balls 46 each define passages for precisely receiving and universally supporting the therapeutic probe PB. Thus, when the holders 40 and 42 are set in specific positions, a path is defined for the probe passing through the balls 46.

In addition to supporting the structure of the arch 32 (for holding the probe PB), the ring 24 supports a reference apparatus (rods 22) for identifying the location of each scan slice. The localizing rods 22 are carried on the ring 24 and include a set of vertical rods 48, 50, 52, and 54. Diagonal rods 58, 60, and 62 extend between the tops and bottoms of certain vertical rods along the ring 24. As indicated above, these rods or graphic reference means provide marks or indicia 64 (FIG. 1) in the display of each scan slice so as to locate the scan slice with reference to the frame 10.

Reference will now be to the somewhat graphic FIG. 4 in pursuing an explanation of the locating operation. Each set of localizing rods is generalized and may be considered as a pair of vertical rods A and C with the diagonal rod B extending from the top of the vertical rod A to the bottom of the vertical rod C. An exemplary scan slice 66 is depicted graphically in FIG. 4 as a plane which passes through the rods A, B, and C. Thus, the sections of the rods will appear in the data and the display of a scan slice to provide landmarks. Such indicia serves as a basis for computations to transform slice data from the slice coordinate system to the frame coordinate system as well as the reverse thereof. Of course, the set of rods A, B, and C is similar to each of three sets of such rods as illustrated in FIG. 3.

The represented scan slice through the rods A, B, and C produces representative ellipses that are similarly identified as ellipses A, B, and C as graphically indicated in FIG. 4. The designated center points are the respective centroids of the ellipses A, B, and C. The distance from the point A to the point C is $d_{ac}$ (as indicated). The distance from the plane-intersect point B to the point C is $d_{bc}$ (as indicated). The length of the rod B is designated as $L_{ac}$ while the distance along the rod B from the bottom of the rod C to the point of the intersection with the plane 66 is designated as $L_{bc}$. As $d_{ac}$, $d_{bc}$, and $L_{ac}$ are known, $L_{bc}$ may be calculated from similar triangles, e.g.:

$$\frac{L_{bc}}{L_{ac}} = \frac{d_{bc}}{d_{ac}}$$

therefore, $$L_{bc} = \frac{L_{ac} \cdot d_{bc}}{d_{ac}}$$

It is noteworthy that precise calculations depend to some extent on the precision of calculating the centroids of the ellipses A, B, and C (FIG. 4). This computation is performed within the data processing apparatus 18 (FIG. 1). As disclosed below, the ellipses are marked by manipulating a cursor on the display of the console 16. Then, computation involves starting with the pixel at which the ellipse was marked by the cursor and locating a contiguous region of pixels having attenuation coefficients corresponding to the acrylic plastic of the frame 10 as detected by the scanner 12. The centroid of these pixels is then taken to be the centroid of the ellipse. Due to random noise, pixels actually belonging to the ellipse, but having attenuation coefficients outside a chosen range for acrylic plastic will not be included in the centroid calculation. If these pixels are not evenly distributed about the actual centroid of the ellipse, the calculated centroid will be incorrect. For example, consider an ellipse comprised of thirty pixels. If six of the pixels concentrated at one edge of the ellipse are not included in the centroid calculation the resulting centroid will be incorrect by approximately 0.6 pixel.

Determining $L_{bc}$ enables the calculation of a representative point B' on the frame which corresponds to the point B in the scan slice 66. The points B and B' are determined for each of the three sets of localizing rods on the frame 10 and accordingly (as three points of a plane) specify the relationship between the scan slice of concern and the frame. That is, the three points B' define the spatial orientation of a plane through the frame 10 with respect to the patient's cranium. Since each scan slice contains three points B, the slice need not be parallel either to other slices or to the base of the frame 10. Of course, deviations may occur as a result of movement of the cranium between scan slices with respect to the scanner. Thus, each scan slice lies in its own coordinate system.

To relate the scan coordinate systems to the frame coordinate system, the three pairs of points B and B' are employed to calculate a pair of matrices. This approach eliminates the need to fix the patient's cranium to the scanner and allows movement of the patient's head after successive scans. The structure employed for the transformations is considered in greater detail below.

In view of the above introduction, an appreciation of the system may now best be accomplished by pursuing a description of the manner in which the system is employed to treat a malady. Accordingly, assume a patient with a brain tumor is to be treated by using the system as disclosed herein. In explaining the operations of the system for such treatment, reference will be made to components and structures described above as well as additional structures introduced and designated below.

The assumed patient 14 (FIG. 1) first receives the frame 10 (FIG. 3) which is rigidly affixed to the cranium as by screw fastener brackets 11. Wearing the frame 10, a brain scan is taken of the patient 14, by means of radiation, represented by the dashed line 70. The operation and structure of CT scanners is well known in the prior art which affords several specific forms that may be employed as the CT scanner 12. Somewhat similarly, visual display console apparatus for use with such scanners are also well known in the prior art and are readily available for embodiment as the console 16. During the brain scan operation, a control unit 72 provides system control upon the depression of a selector button 74 to accommodate the somewhat conventional scanning operation. Other selections involve a button 76 for designating display locations during input operations and a selection button 78 to initiate data processing.

With the completion of each scan slice, the designating button 76 is depressed and a set 80 of directional controls are actuated to visually position a cursor 82 at selected locations for marking the indicia 64 (indicative of the rods 22). Specifically, for example, during the "designate" stage of operation, the set 80 of directional controls would be actuated to position the cursor 82 at each of the indicia 64. At such locations of the cursor 82, the keyboard would be used to specify the indicia 64 as ellipses, e.g. ellipses A, B, or C as explained above.

Repeating the operation cyclically, each scan slice is reduced to data indicating a section through the patient's cranium along with the indicia 64 designating the location of the scan slice. Data representative of such a display is provided from the scanner 12 to the data processing apparatus 18 for registration therein.

The data processing apparatus 18 is shown in greater detail in FIG. 5. The data from the scanner 12 is provided to a processing unit 84 which performs the computations described above for the development of signals representative of B and B'. That is, when a scan slice is completed, the "designate" button 76 is depressed and the rod markings are identified. Thereafter, the "compute" button 78 is depressed and buttons of a keyboard 90 are selectively depressed to command the transfer of the display data to the computing apparatus and specifically to the unit 84 (FIG. 5) for refinement and finally registration is a designated address in the storage 86. The complete brain scan (normally including a multiplicity of scan slices) is concluded, as described above, taking each scan slice as an individual data set and recording it along with its associated locating signals for values B' in the storage 86. After the completion of the brain scan, various slices may be recalled for display and study with the system in a "designate" mode. The keyboard 90 designates address locations of the slices in the storage 86. Such operations facilitate the selection of the particular slice which contains the target T (FIG. 1). Of course, a number of medical considerations may involve the selection of the target T which considerations are not here pertinent. However, having made the selection, the cursor 82 is activated and directed for identifying the precise two-dimensional coordinates of the target point $P_t$ in the selected scan slice. The designation is then recorded by selectively actuating the keyboard 90. Another point $P_p$ is also designated which is first determined by selecting a slice S1 (FIG. 2(a)) within which the cursor 82 is directed to specify the point $P_p$ and thereby determine the path PA.

The computation of the path PA involves relating the points $P_t$ and $P_p$ to the coordinate system of the frame 10, defining the line between such points then simply computing the settings for the rings 24 and 28 (FIG. 3) along with those for the holders 40 and 42. Traditional computer graphics computation patterns have been used for such processing. Specifically, the target points $P_t$ (scan S3, FIG. 2(b)) and $P_p$ (scan S1) have been defined and are now contained in the storage 86 preparatory to conversion. The data defining these points is processed during a timing interval T2 established by the control unit 86 to activate a data sequence 92 which in turn supplies the data to a transform unit 94. Generally, transform systems are well known in the prior art as described at length (along with other computer graphics structures) in a book *Principles of Interactive Computer Graphics*, published in 1973 by McGraw-Hill, Inc., specifically, see Chapter 8.

The transform computation employed in an operating embodiment hereof involves a pair of matrices that are used to relate the coordinate system of a given scan slice to the frame coordinate system. One matrix, hereinafter called the frame matrix and represented by [F] transforms points from a scan slice coordinate system to the frame coordinate system. Another matrix, hereinafter called the slice matrix and represented by [S], transforms points in the frame coordinate system into the scan slice coordinate system.

The slice coordinate system is assumed to lie in an x, y plane with z equal to any non-zero constant. For subsequent computations, z is arbitrarily set to a value of one. Thus, any point in this plane may be represented as (x, y, 1) where x and y are the column and row, respectively, of the point in the scan slice. The frame coordinate system is a three-dimensional coordinate system. Any point in this coordinate system may be represented as (x',y',z').

The three points B as described above in the slice coordinate system are used as the elements of a matrix herein represented by [B]. The three points B' in the frame coordinate system are used as the elements of a matrix hereinafter represented by [B']. The matrix [B] may be related to the matrix [B'] by the following linear transformation:

$$[B][F] = [B']$$

which may alternately be represented with the matrices designated as:

$$\begin{bmatrix} x_1 & y_1 & 1 \\ x_2 & y_2 & 1 \\ x_3 & y_3 & 1 \end{bmatrix} \begin{bmatrix} f_{11} & f_{12} & f_{13} \\ f_{21} & f_{22} & f_{23} \\ f_{31} & f_{32} & f_{33} \end{bmatrix} = \begin{bmatrix} x_1' & y_1' & z_1' \\ x_2' & y_2' & z_2' \\ x_3' & y_3' & z_3' \end{bmatrix}$$

where $f_{11} \ldots f_{33}$ are the elements of matrix [F] which are to be calculated. These elements are easily calculated by rearranging the above concise equation form:

$$[F] = [B]^{-1}[B']$$

Once the frame matrix elements are known, the matrix may be used to transform any point from the slice coordinate system into the frame coordinate system using the following relation:

$$[xy1][F] = [x'y'z']$$

The slice matrix [S] is the inverse of the frame matrix. Its elements may be calculated by either inverting the frame matrix:

$$[S] = [F]^{-1}$$

or by inverting the above equation expressing [F]:

$$[S] = [B']^{-1}[B]$$

Once the slice matrix elements are known, the matrix may be used to transform any point from the frame coordinate system into the slice coordinate system using the following relation:

$$[x'y'z'][S] = [x''y''z'']$$

Utilizing the matrix transformation, as well known and widely used in computer graphics, the data processing apparatus 18 performs the localization illustrated in FIG. 2. That is, the transform unit 94 (FIG. 5) embodies structure to transform individual point locations into related point locations that are referenced to the frame 10.

The first step in computing the stereotactic frame settings for the holders 40 and 42 (FIG. 3) is to transform both the points $P_t$ (target) and $P_p$ (passage point) from their respective slice coordinate systems (illustrated in FIG. 2(b)) into the frame coordinate system (illustrated in FIG. 2(c)) as points $P_t'$ and $P_p'$. The transform unit 94 accomplishes the conversion by multiplying each point by the frame matrix calculated for its respective scan slice as indicated in the above equations. The computations occur during the timing interval T2 with the results being preserved in a memory of the arithmetic unit 98. The resulting transformed points $P_t'$ and $P_p'$ are then used to describe the path PA (FIG. 2(c)) for the therapeutic probe. The use of two points to define a path is well known and widely used in computer graphics systems; for example, see U.S. Pat. No. 3,639,736.

Utilizing conventional computer structure and techniques, from the defined path, the arithmetic unit 98 calculates the frame settings in accordance with the geometry of the frame. In this regard it is to be noted that the computations will depend on the structure of the frame 10, which may assume a wide variety of different possible configurations, the function being simply to guide a therapeutic probe to follow a predetermined path PA. A frame 10 as disclosed herein has been used for substantial experimentation; however, although results were impressive, it is to be appreciated that other forms of frames may well be employed in the system.

After the arithmetic unit 98 has computed data defining the path PA (FIG. 2(c)) the next operation involves displaying each of the scan slices and exhibiting a market at the point where the probe would pass through the slice so that the physician may decide whether or not the tentative path PA should be pursued. This calculation involves the slice transformation matrix developed for each of the scan slices. The two points $P_t'$ and $P_p'$ describing the path in the frame coordinate system are multiplied by the slice matrix as indicated in the above equations to transform them from the frame coordinate system into the slice coordinate system. This operation occurs during a stage defined by the control 88 as T3 in response to an input command on keyboard 90. As illustrated (FIG. 5), the data moves in a reverse direction through the transform unit 94. The transformed points $P_t''$ and $P_p''$ are then used to define the punctures or penetration points in each of the scan slices. Again, such data is processed in the slice coordinate system as illustrated in FIG. 2(d). For example, the point I where the path PA intersects the slice S2 may be established by setting $z=1$ and solving for x and y.

When the data is complete for each scan slice, the slices are displayed on the console 16 for individual consideration. If the proposed path is rejected, the process is repeated to select a fresh path, otherwise the path is approved for use. Note that during this period, the patient is mobile and can be made relatively comfortable although wearing the frame 10.

For the execution of the path PA, the patient is taken to surgery with the frame 10 (FIG. 3) set to guide the probe PB along the path PA. These settings involve the angular displacements of the rings 24 and 28 as well as the placement of the holders 40 and 42, all in accordance with the computed indications. The settings are verified, then a relatively small access hole is made in the cranium to pass the probe PB. The probe is then inserted to the computed depth and the treatment is performed. Again, as noted above, surgery may be done or biopsy taken in the scanner. Thus, several techniques provide alternatives.

With the completion of the surgical procedure, the probe is removed, the incision is closed, and normally the frame 10 is removed. Of course, the recovery period will normally be indicative of the success of an individual surgery; however, according to present indications, use of the system as described above will assist considerably in obtaining a desirable probe placement.

Although the above explanation of an illustrative embodiment is deemed to effectively establish a basis for terminology in claims hereof, the following dictionary definitions are submitted for possible further clarification. Specifically, the following definitions are taken from *Webster's Third New International Dictionary*, 1961 by G. & C. Merriam Co.:

"probe": "a surgical instrument that consists typically of a light, slender, fairly flexible pointed metal instrument that is used typically for locating a foreign body"

"universally": "so as to be universal"

"universal": "adapted or adjustable to meet varied requirements of use"

"attaining (attain)": "to reach or come to by progression or motion"

"target": "something that is or may be aimed at"

"graphic": "of, relating to, or represented by graphs, diagrams, lines or similar means"

"scanning (scanner)": "minute, thorough, critical or judicial examination".

It is to be recognized that various forms of the frame 10 may be employed to provide: attachment to the cranium, reference indicia, and a holding guide structure. Furthermore, various forms of scanners, display devices, and data processing components also can be utilized to accomplish the ends of this invention. Consequently, the scope hereof should generally be as defined by the claims as set forth below.

What is claimed is:

1. A method of treating the interior of a body at a specific target location, comprising:
   rigidly affixing a support means to the body;
   fastening a graphic reference means to said support means to provide varying data to a computed tomography (CT) scanner to index scan in relation to said support means;
   scanning said body and said support means with a computed tomography (CT) scanner to provide data representative of scan slices through said body and said reference means; and
   computing a course to said target location using said data representative of scan slices.

2. A method according to claim 1 further including the step of fastening a probe means to said support means and aligning said probe means in accordance with the computed course to attain said target location.

3. In association with a computed tomography (CT) scanner and a probe means for attaining a target location in a body, the improvement which comprises an apparatus for developing data to compute a course to said target location comprising:
   support means adapted to be rigidly connected to said body for providing a frame coordinate reference;
   graphic reference means supported by said support means and including diagonal members with respect to said frame coordinate reference whereby upon scanning of said body and said graphic reference means by said scanner, slice data is obtained which includes data for referencing such data to said support means.

4. Stereotactic frame apparatus adapted for use in performing stereotactic surgery with an X-ray CT scanner, said stereotactic frame apparatus comprising:
   a stereotactic frame defining a three-dimensional coordinate system which can be fixed with respect to the anatomy of a living patient,
   said stereotactic frame including mechanism for positioning a desired surgical device within said anatomy at any desired location defined in terms of said three-dimensional coordinate system, and X-ray detectable fiducial marker means associated with said stereotactic frame defining at least three noncollinear points within each planar cross-section therethrough, said marker means including means for determining the three-dimensional coordinates of said three points in each said cross-section whereby a scan in any single plane provides the three-dimensional coordinates of said three noncollinear points.

5. Apparatus as in claim 4 wherein said X-ray detectable fiducial markers comprise:

a member having an X-ray detectable feature which intersects any said cross-section at a location which varies depending upon the relative disposition of the cross-section.

6. An improved stereotactic surgery frame of the type defining a three-dimensional coordinate system which can be fixed with respect to the anatomy of a living patient and which can thereafter position a desired surgical device within such anatomy at any desired location defined in terms of said three-dimensional coordinate system, said improvement comprising:

X-ray detectable fiducial markers physically associated with said frame and defining at least three measurable noncollinear fiducial points, each having predetermined visually determinable three-dimensional coordinates within a single cross-section depiction taken through the combination of said anatomy and of said frame and its associated fiducial markers.

7. An improvement as in claim 6 wherein said fiducial markers comprise:

a member having a detectable feature which intersects any desired cross-sectional depiction at a location which varies depending upon the relative disposition of the cross-section.

8. A method to facilitate stereotactic surgery, said method comprising the steps of:

fixing a stereotactic surgical frame, having a first predetermined three-dimensional coordinate system, with respect to living tissue, scanning the combination of said frame and living tissue with penetrating radiation to provide a cross-sectional depiction thereof in a single plane which includes a desired anatomical target within said living tissue, determining the three-dimensional coordinates of said target with respect to a second predetermined three-dimensional coordinate system, determining the three-dimensional coordinates of each of at least three non-collinear points located within said cross-sectional depiction in a single plane, both with respect to the three-dimensional coordinate system of said frame and with respect to said second three-dimensional coordinate system, and using said determined coordinates to calculate the coordinates of said target with respect to the three-dimensional coordinate system of said frame.

9. A method as in claim 8 wherein said scanning step is performed with an X-ray CT scanner.

10. A method as in claim 8 wherein said fixing step includes the attachment of X-ray detectable fiducial markers to said frame.

11. A method as in claim 8 wherein said second-mentioned determining step includes measurement of relative distances between detectable features associated with said frame at predetermined relative locations and present in said cross-sectional depiction.

12. Apparatus for performing three-dimensional stereotactic surgery within the anatomy of a living patient, said apparatus comprising:

a tomographic scanner having a programmable data processing computer, a CRT display for depicting the relative densities of elemental volumes with a desired planar cross-sectional slice of matter appropriately placed within the CT scanner, and an operator console for entering data and/or instructions into said computer and for identifying the location and relative positional coordinates of any desired element or portion of said slice;

a rigid frame fixably securable with respect to said anatomy and defining a multi-dimensional coordinate system in which surgical devices can be precisely positioned;

said frame including plural detectable features which if included as a portion of a single said slice of matter in a single plane, will be represented in said depiction of said cross-sectional slice as a respectively corresponding set of at least three functional points in the plane having predetermined known or readily determinable three-dimensional frame coordinates; and said computer being programmed to compute the three-dimensional frame coordinates of any desired anatomical target depicted within said slice as a function of the frame coordinates of said fiducial points and of the relative positional coordinates of said target and said fiducial points within said CRT display.

13. Apparatus as in claim 12 wherein said rigid frame includes at least one detectable feature disposed along a path connecting dissimilar portions of similar spaced-apart frame structures.

14. Apparatus as in claim 12 or 28 wherein said rigid frame includes an inclined rod connected between dissimilar portions of two spaced-apart parallel posts.

15. A method to facilitate stereotactic surgery, said method comprising the steps of:

fixing a stereotactic surgical frame, having a first predetermined multi-dimensional coordinate system, with respect to living tissue, scanning the combination of said frame and living tissue with penetrating radiation to provide a cross-sectional depiction thereof in a single plane which includes a desired anatomical target within said living tissue, determining the three-dimensional coordinates of said target with respect to a second predetermined multi-dimensional coordinate system, determining the three-dimensional coordinates of each of plural points located within said cross-sectional depiction, both with respect to the first multi-dimensional coordinate system of said frame and with respect to said second multi-dimensional coordinate system, and using said determined three-dimensional coordinates to calculate the three-dimensional coordinates of said target with respect to the multi-dimensional coordinate system of said frame.

16. A method as in claim 15 wherein said scanning step is performed with an x-ray CT scanner.

17. A method as in claim 15 wherein said fixing step includes the attachment of x-ray detectable fiducial markers to said frame.

18. A method as in claim 15 wherein said determining step includes measurement of relative distances between detectable features associated with said frame at predetermined relative location and present in said cross-sectional depiction.

19. An improved stereotactic surgery frame of the type defining a multi-dimensional coordinate system which can be fixed with respect to the anatomy of a living patient and which can thereafter position a desired surgical device within such anatomy at any desired location defined in terms of said multi-dimensional coordinate system, said improvement comprising:
fiducial markers physically associated with said frame and defining at least three unique non-collinear measurable fiducial points having determinable three-dimensional coordinates with respect to said frame with a single planar cross-sectional depiction taken through the combination of said anatomy and of said frame and its associated fiducial markers.

20. Apparatus for use in performing stereotactic surgery, said apparatus comprising:
an X-ray CT scanner capable of measuring relative X-ray absorption within elemental volumes of a desired planar cross-section of the anatomy of a living patient and which CT scanner also defines a first multi-dimensional CT scanner coordinate system relative to its own geometrical structure for locating specific anatomical positions with said planar cross-section relative to said first coordinate system,
a stereotactic frame defining a second multi-dimensional coordinate system which can be fixed with respect to the anatomy of a living patient,
said stereotactic frame including mechanism for positioning a desired surgical device within said anatomy at any desired location defined in terms of said second multi-dimensional coordinate system, and
X-ray detectable fiducial markers associated with said stereotactic frame defining plural points within each of said planar cross-sections, each point having determinable coordinates in both said first and said second coordinate systems
said CT scanner including means for transforming the measured CT scan coordinates in three dimensions of a desired portion of the anatomy to corresponding three-dimensional coordinates in said second coordinate system thereby facilitating the use of said stereotactic frame during stereotactic surgery.

21. Stereotactic frame apparatus adapted for use in performing stereotactic surgery, said apparatus comprising:
an X-ray CT scanner means capable of measuring relative X-ray absorption within elemental volumes of a desired cross-section of the anatomy of a living patient and which CT scanner means defines a first three-dimensional CT scanner coordinate system relative to its own geometrical structure for locating specific anatomical positions within said cross-section relative to said first coordinate system,
a stereotactic frame defining a second three-dimensional coordinate system which can be fixed with respect to the anatomy of a living patient,
said stereotactic frame including mechanism for positioning a desired surgical device within said anatomy at any desired location defined in terms of said second three-dimensional coordinate system,
X-ray detectable fiducial markers associated with said stereotactic frame defining at least three non-collinear points within each of said cross-sections, each point having determinable coordinates in both said first and said second coordinate systems such that the measured CT scan coordinates of a desired portion of the anatomy can be transformed to corresponding coordinates in said second coordinate system thereby facilitating the use of said stereotactic frame during stereotactic surgery,
said frame including spaced-apart posts; and
said markers including a rod extending between dissimilar portions of pairs of said spaced-apart posts.

22. A system for specifying a path into a body as to direct a surgical probe, comprising:
support means adapted to be rigidly connected to said body;
a computed tomography (CT) scanner means for scanning through the body in the proximity of said support means to product graphic data representative of cross-sectional scan slices through said body defining a target location;
graphic reference means supported by said support means to be within said scan slices and for providing reference data for said individual scan slices with respect to said support means; and
probe means supported by said support means and setable to penetrate said body along a path in accordance with said graphic data and said reference data to attain said target location.

23. A system according to claim 22 further including means for displaying said graphic data and said reference data.

24. A system for specifying a path into a body as to direct a surgical probe, comprising:
support means adapted to be rigidly connected to said body;
scanner means for scanning through the body in the proximity of said support means to produce graphic data representative of scan slices through said body defining a target location;
graphic reference means including rods to extend diagonally with respect to said support means and supported by said support means to be within said scan slices and for providing reference data for said individual scan slices with respect to said support means; and
probe means supported by said support means and setable to penetrate said body along a path in accordance with said graphic data and said reference data to attain said target location.

25. A system for specifying a path into a body as to direct a surgical probe, comprising:
support means adapted to be rigidly connected to said body;
scanner means for scanning through the body in the proximity of said support means to produce graphic data representative of scan slices through said body defining a target location;
graphic reference means supported by said support means to be within said scan slices and for providing reference data for said individual scan slices with respect to said support means;
probe means supported by said support means and setable to penetrate said body along a path in accordance with said graphic data and said reference data to attain said target location; and a data processing means for computing settings for said path on the basis of said graphic data and reference data and further including means to transform data defining said path to a coordinate system referenced to said scan slices.

26. A system for specifying a path into a body as to direct a surgical probe, comprising:

support means adapted to be rigidly connected to said body;

scanner means for scanning through the body in the proximity of said support means to produce graphic data representative of scan slices through said body defining a target location;

graphic reference means supported by said support means to be within said scan slices and for providing reference data for said individual scan slices with respect to said support means;

probe means supported by said support means and setable to penetrate said body along a path in accordance with said graphic data and said reference data to attain said target location; and data processing means to transform data from a coordinate system referenced to said support means to a coordinate system, or coordinate systems, referenced to said graphic data representative of said body.

27. A system for specifying a path into a body as to direct a surgical probe, comprising:

support means adapted to be rigidly connected to said body;

scanner means for scanning through the body in the proximity of said support means to produce graphic data representative of scan slices through said body defining a target location;

graphic reference means supported by said support means to be within said scan slices and for providing reference data for said individual scan slices with respect to said support means;

probe means supported by said support means and setable to penetrate said body along a path in accordance with said graphic data and said reference data to attain said target location; and data processing means to transform data from a coordinate system referenced to said support means to coordinate systems referenced to said scan slices.

28. A system for specifying a path into a body as to direct a surgical probe, comprising:

support means adapted to be rigidly connected to said body;

scanner means for scanning through the body in the proximity of said support means to produce graphic data representative of scan slices through said body defining a target location;

graphic reference means supported by said support means to be within said scan slices and for providing reference data for said individual scan slices with respect to said support means;

probe means supported by said support means and setable to penetrate said body along a path in accordance with said graphic data and said reference data to attain said target location; and data processing means to transform data from a coordinate system, or coordinate systems, referenced to said graphic data representative of a part of said body to a coordinate system referenced to said support means.

29. A system for specifying a path into a body as to direct a surgical probe, comprising:

support means adapted to be rigidly connected to said body;

scanner means for scanning through the body in the proximity of said support means to produce graphic data representative of scan slices through said body defining a target location;

graphic reference means supported by said support means to be within said scan slices and for providing reference data for said individual scan slices with respect to said support means;

probe means supported by said support means and setable to penetrate said body along a path in accordance with said graphic data and said reference data to attain said target location; and data processing means to transform data from coordinate systems referenced to said scan slices to a coordinate system referenced to said support means.

30. A system for specifying a path into a body as to direct a surgical probe, comprising:

support means adapted to be rigidly connected to said body;

scanner means for scanning through the body in the proximity of said support means to produce graphic data representative of scan slices through said body defining a target location;

graphic reference means supported by said support means to be within said scan slices and for providing reference data for said individual scan slices with respect to said support means;

probe means supported by said support means and setable to penetrate said body along a path in accordance with said graphic data and said reference data to attain said target location; and data processing means to transform said graphic data representative of a part of said body from a coordinate system referenced to said graphic data representative of a part of said body to a coordinate system referenced to said support means.

31. A system for specifying a path into a body as to direct a surgical probe, comprising:

support means adapted to be rigidly connected to said body;

scanner means for scanning through the body in the proximity of said support means to produce graphic data representative of scan slices through said body defining a target location;

graphic reference means supported by said support means to be within said scan slices and for providing reference data for said individual scan slices with respect to said support means;

probe means supported by said support means and setable to penetrate said body along a path in accordance with said graphic data and said reference data to attain said target location; and data processing means further including means to transform data defining said path from a coordinate system referenced to said support means to coordinate systems referenced to each of said scan slices.

* * * * *